United States Patent [19]

Fleenor et al.

[11] Patent Number: 5,549,618

[45] Date of Patent: Aug. 27, 1996

[54] KNOT TYING METHOD AND APPARATUS

[75] Inventors: RIchard P. Fleenor, Englewood; Daniel P. Bryce, Westminster, both of Colo.

[73] Assignee: Coral Medical, Englewood, Colo.

[21] Appl. No.: 391,913

[22] Filed: Feb. 21, 1995

Related U.S. Application Data

[63] Continuation-in-part of Ser. No. 182,609, Feb. 18, 1994.

[51] Int. Cl.⁶ .................................. A61B 17/00
[52] U.S. Cl. .................. 606/148; 606/139; 606/167; 606/170; 112/169
[58] Field of Search .................................. 606/139, 144, 606/145, 148, 167, 170, 171, 180; 289/17; 112/169, 80.03

[56] References Cited

U.S. PATENT DOCUMENTS

| | | | |
|---|---|---|---|
| 3,995,619 | 12/1976 | Glatzer | 606/171 |
| 4,038,988 | 8/1977 | Perisee | 606/167 |
| 5,112,299 | 5/1992 | Pascaloff | 606/170 |
| 5,397,326 | 3/1995 | Mangum | 606/148 |
| 5,423,837 | 6/1995 | Mericle et al. | 606/148 |

Primary Examiner—Stephen C. Pellegrino
Assistant Examiner—Jeffrey A. Schmidt
Attorney, Agent, or Firm—Beaton & Folsom

[57] ABSTRACT

A method and apparatus for placing and tying a knot such as laparoscopy knot. A knot pusher assembly including an outer tube and an inner tube are positioned, and a plunger assembly is plunger through the knot pusher assembly. The plunger assembly includes a knot carrier having an at least partially formed knot with a free end. The free end is placed around the object to be tied and grasped with a clamp. The knot is released from the knot carrier and the free end is pulled back through the partial knot to complete and tighten the knot. The knot is tightened and placed using the knot pusher assembly, and the free end is cut by placing it into aligned slots on the outer tube and inner tube, and rotating the inner tube in relation to the outer tube to unalign the slots.

3 Claims, 5 Drawing Sheets

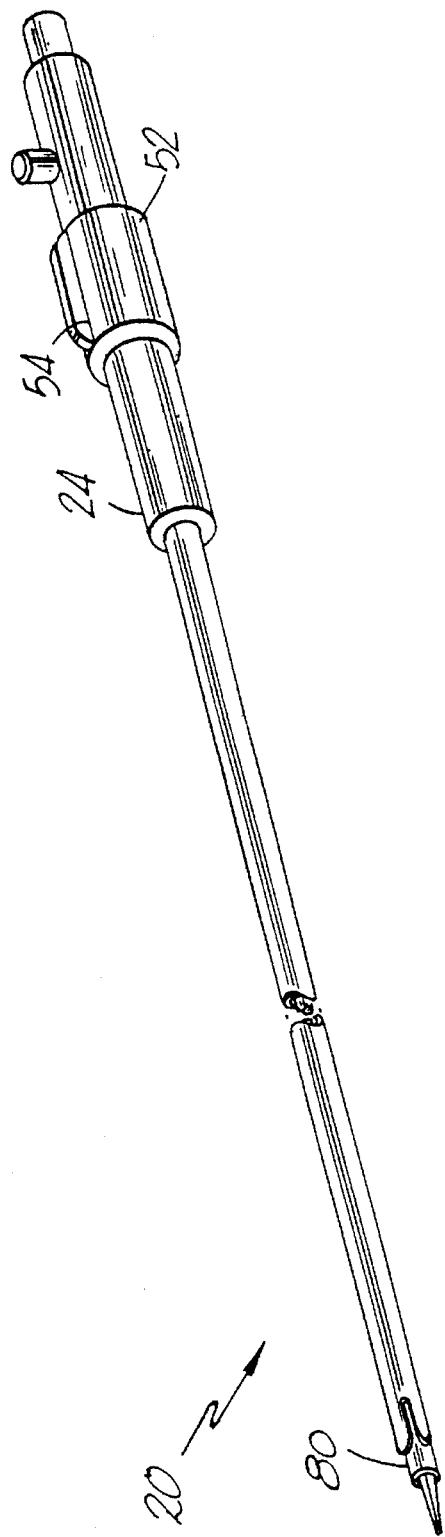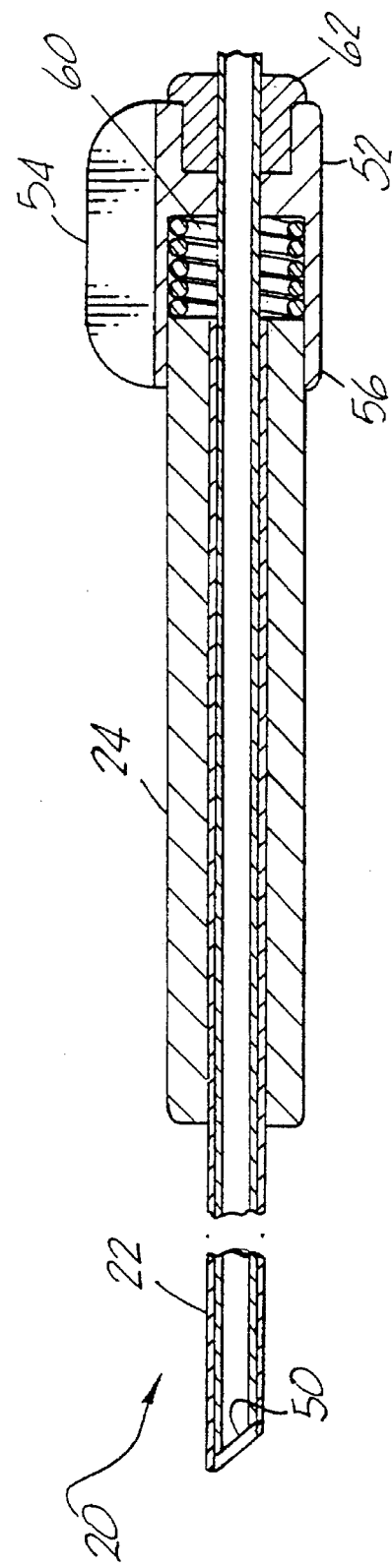

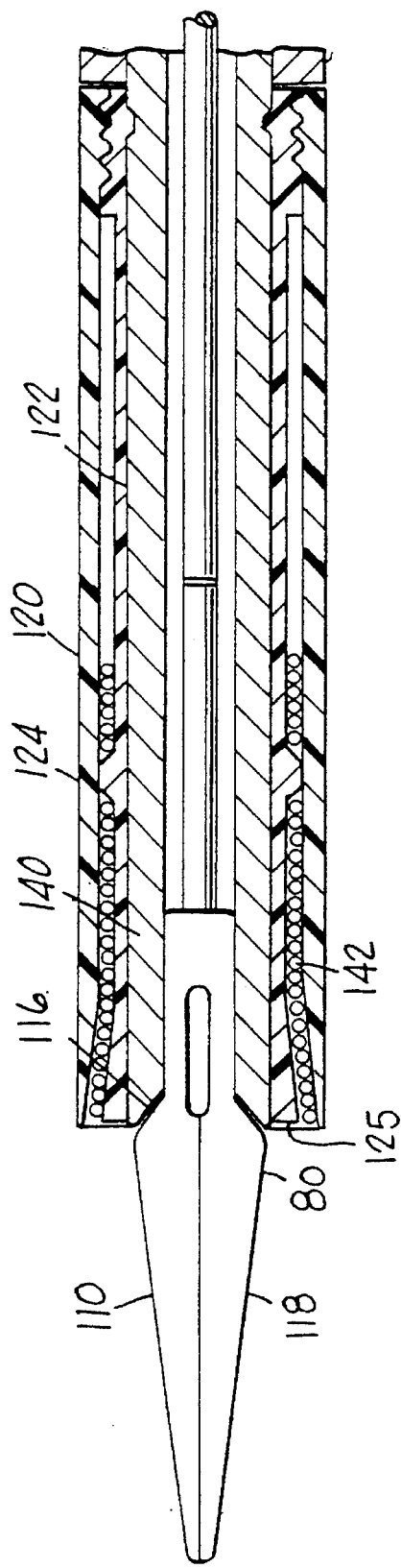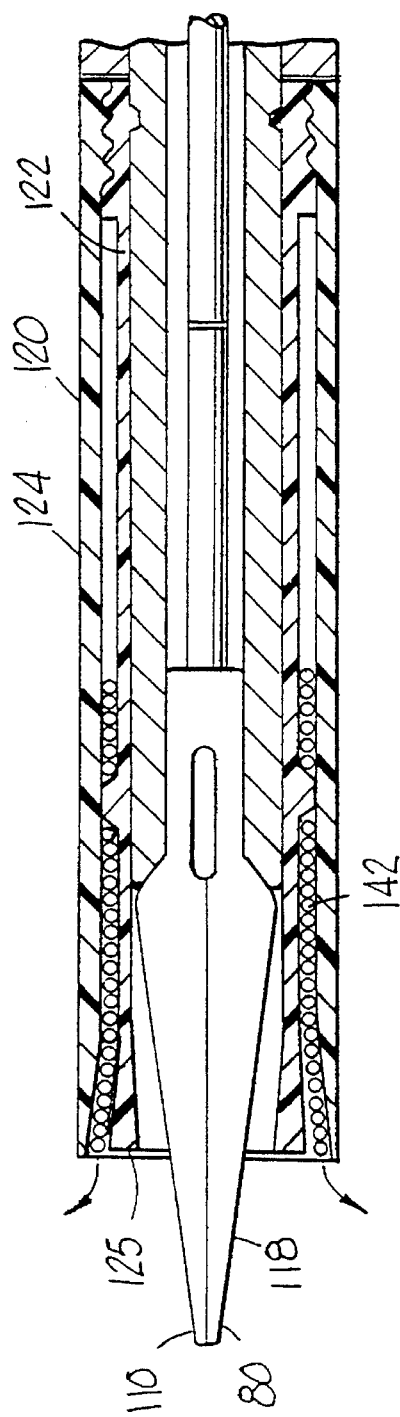

KNOT TYING METHOD AND APPARATUS

This application is a continuation in part of application Ser. No. 08/182,609 dated Feb. 18, 1994.

FIELD OF THE INVENTION

The present invention relates to the broad field of knot tying, and particularly knot tying in the context of medicine such as the tying of sutures. More specifically, the invention has special applicably to the tying of sutures and other knots in the field of laparoscopic surgery.

BACKGROUND OF THE INVENTION

Knot tying and suturing as a method to approximate tissue is a critical element of surgery. Skill in knot tying is so basic to surgery that medical students learn knot tying early in their studies, and they routinely practice tying various kinds of knots with one hand or both hands.

In laparoscopic procedures, the tying of sutures and other knots is especially difficult and it is not uncommon for the tying of a single knot to require an hour or more. In laparoscopy, there is no tactile sense to the surgeon because of the surgeon's lack of direct contact with the tissue, since the surgeon's sense of feel is reduced by the imposition of the laparoscopic instruments. Further, the surgeon is unable to view directly the site of the surgery, but instead must rely upon a two-dimensional video screen which both magnifies the site and eliminates the opportunity for any depth perception.

Another difficulty is presented by the fact that laparoscopic surgery necessarily is conducted in a confined space, and the instruments are preferably positioned in this confined space in a particular orientation in relation to one another and in relation to the patient. For example, it is desirable that within this confined space, the instruments not be too close together or too far apart, that they be visible through the laparoscope, and that they enter the field of view of the laparoscope tangentially rather than coaxially so that they do not obstruct the view too much. It is also desirable that the instruments advance out of their sheaths toward the video screen and away from the laparoscope in order to avoid the surgeon having to operate under "mirror vision". Finally, procedures employing a single operating port encourage the surgeon to use the dominant hand to manipulate the instrument in the port while using the other hand merely to stabilize the laparoscopic sheath. However, knot tying typically requires both hands, and so an assistant or a device is then necessary to stabilize the sheath while both the surgeon's hands tie the knot.

Suturing and other knot tying are applicable to many different laparoscopic procedures. In laparoscopic cholecystectomy, the cystic duct or artery can be ligated using manual suturing or knot tying techniques rather than an automatic clip. In a laparoscopic appendectomy, the surgeon can use slip knots rather than using a disposable linear stapler. Although laparoscopic staplers have been developed, laparoscopic sutures and other knots will still be needed for many purposes such as closing defects in a staple line, placing purse-string sutures for end-to-end stapling, closing mesenteric defects, and ligating large blood vessels.

Knots used in laparoscopy may be tied either intracorporeally or extracorporeally. Internal knotting requires a high level of expertise by the surgeon, and normally requires at least two operating cannulae and associated graspers. For a square knot, a loop is made in a first end of the material using the first grasper; the second grasper is inserted through the loop and used to grasp the second end; the second end is pulled through the loop to produce a flat knot; another loop is made in the first end of the material using the first grasper; the second grasper is inserted through that loop and used to grasp the second end; and the second end is pulled through that loop to produce an opposing flat knot. The resulting square knot can then be tightened with the two graspers. The first throw may be a simple overhead knot or may be a surgeon's knot. Additional throws may be applied over the second throw to provide additional security. It is important that sequential throws are in opposite directions to avoid producing a "granny" knot.

Many other types of knots are possible depending on the characteristics of the material used, the dexterity of the surgeon, and the circumstances at the suture site. Many knots in laparoscopy are slip knots of some kind to allow the knot to be cinched against the sutured material. These include the Roeder knot, a clinch knot and so-called "hangman's" knots.

Extracorporeally tied knots are obviously much easier to tie than intracorporeally tied knots, but extracorporeally tied knots can be very difficult to place effectively. A number of devices have been developed to assist in placing an extracorporeally tied knot including the "Clarke" ligator, the "Weston" ligator (see "A New Cinch Knot", Obstetrics & Gynecology, Vol. 78, No. 1, July 1991, 144–47) and other devices. See, e.g. "An Improved Needleholder for Endoscopic Knot Tying", Fertility and Sterility, Vol. 58, No. 3, Sept. 1992, 640–42; "Roeder Knot for Tight Corners in Conventional Abdominal Surgery", J. R. Coll. Surg. Vol. 36, Dec. 1991, 412; "A Simple Method for Ligating with Straight and Curved Needles in Operative Laparoscopy", Obstetrics and Gynecology, Vol. 79, No. 1, Jun. 1992, 143–47. Most of the devices for placing an extracorporeally tied knot fall into the category of "knot pushers". A knot is formed extracorporeally and is pushed through the cannula by sliding it down the material using a device that engages the knot. The Clarke ligator mentioned above was one of the first knot pushers. It simply consists of a grasping end and an end opposite the grasping end with an open ring. It engages the knot by passing the material through the opening in the ring.

There are also a number of patented knot pushers, including those described in U.S. Pat. Nos. 5,234,445 by Walker, 5,234,444 by Christondias, 5,217,471 by Burkhart, 5,192,287 by Fournier, 5,163,946 by Li, 5,129,912 by Noda, 5,133,723 by Li, 5,084,058 by Li, 3,871,379 by Clarke, and 2,012,776 by Roeder. There are also a number of patents directed more toward endoscopic knotters, including U.S. Pat. Nos. 5,234,443 by Phan, 5,211,650 by Noda, 4,961,741 by Hayhurst, 4,923,461 by Caspari, 4,890,614 by Caspari, 4,641,652 by Hatterer, and 4,602,635 by Mulhollan. It is believed that an important limitation to these devices is that they do not include a disposable knot carrier in the manner of the present invention.

SUMMARY OF THE INVENTION

The present invention is a system for placing a pretied extracorporeal knot, with particular but not exclusive application to laparoscopy. The knot may be a slip knot or some other knot, especially a knot that can be formed by passing the free end through a knot body which includes a loop or set of loops.

A device is disclosed which includes a knot pusher assembly that comprises a pusher tube with an inner concentric tube. The pusher tube and inner concentric tube each include a slot, the two slots being aligned with one another to function as scissors. The material is cut by sliding it into the two aligned slots and rotating the inner tube in relation to the pusher tube to unalign the slots to divide the material.

A plunger assembly is slidably received by the inner tube of the knot pusher assembly. The plunger assembly includes a needle clamp at the distal end which is normally closed but can be opened or "sprung" by actuating a clamp actuator at the proximal end. Also at the distal end of the plunger assembly is a carrier holder which holds a knot carrier. The carrier holder is preferably a cylindrical portion of the plunger assembly behind the needle clamp, and the knot carrier is preferably a tubular element that slides and fits snugly onto the carrier holder. The carrier itself includes a sheath which fits over and is concentric with the spool. The outside diameter of the spool is less than the inside diameter of the sheath, so that an annular space is defined between the two. The annular space receives the tied knot or substantially tied knot.

The outer surface of the distal end of the spool is flared radially outward, and the inner surface of the distal end of the sheath is chamfered to receive the flare of the spool. The flared distal end of the spool is also slotted in the longitudinal direction. When the carrier is positioned onto the carrier holder, the carrier holder expands the flared distal end of the spool radially outward toward the sheath to firmly hold in place the tied knot in the annular space between the spool and the sheath. However, when the carrier is displaced by sliding it partway off the carrier holder so that the carrier holder no longer is inside the flared distal end of the spool, then the flared distal end of the spool relaxes and moves radially inward. This relieves the binding force on the tied knot in the annular space between the spool and the sheath, thereby allowing the knot to come out of the carrier. A tubular carrier releaser extends the length of the plunger assembly to accomplish this displacement of the carrier upon actuation by an activator on the plunger assembly proximal end.

The device is operated by inserting the knot pusher assembly into a cannula to a desired site, loading the knot carrier with its pre-tied knot onto the carrier holder of the plunger assembly, and inserting the plunger assembly into the knot pusher assembly. Once the desired suture is made using a needle, or some other knot need is satisfied, the free end of material is grasped with the needle clamp. The knot is then released from the carrier by actuating the carrier releaser actuator to displace the carrier distally so that the distal end of the carrier spool is no longer urged radially outward by the needle clamp. The plunger assembly is then withdrawn from the knot pusher assembly while the knot pusher assembly receives the material in the aligned slots of the pusher tube and inner concentric tube, thereby tightening the knot. The free end of material can be divided by rotating the inner concentric tube in relation to the pusher tube to unalign the slots. The plunger assembly, with the carrier displaced but still on the carrier holder, is then withdrawn from the plunger knot pusher assembly. If desired, another knot or suture can then be made by removing the spent knot carrier from the carrier holder and reloading a new knot carrier onto the carrier holder, and then repeating the procedure.

Although the system is described principally in the preferred embodiment of laparoscopy applications, it can be appreciated that the system is also suitable for many other intracorporeal and extracorporeal applications.

BRIEF DESCRIPTION OF THE DRAWINGS

FIG. 1 shows a perspective view of an apparatus in accordance with the present invention.

FIG. 2 shows a side sectional view of the knot pusher assembly of the invention.

FIG. 11 shows a side sectional view of the distal end of the invention showing the knot carrier in the carrying position.

FIGS. 12A–12F show schematically the process of tying, positioning and trimming a knot in accordance with the process of the present invention.

DETAILED DESCRIPTION OF THE INVENTION

Figure 5:
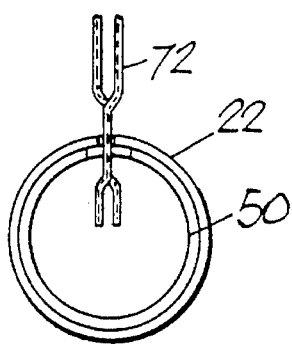
FIG. 5 shows an end view of the distal end of the knot pusher assembly prepared for the cutting of suture material.

An overall view of a preferred embodiment of the invention is shown in FIG. 1, including the knot pusher assembly 20 and the plunger assembly 80. As shown in FIG. 1 and also in more detail in the side sectional views of FIG. 2, the knot pusher assembly 20 includes a pusher tube 22 and an inner concentric tube 50. At the proximal end of the knot pusher assembly 20, the pusher tube is attached to a cylindrical handle 24 and the inner concentric tube 50 is attached to a rotator 52 having a longitudinal, radially extending wing 54. The proximal end of the inner concentric tube 50 extends beyond the proximal end of the pusher tube 22 to allow the connection between the inner concentric tube 50 and the rotator 52. The rotator 52 includes a sleeve 56 which extends from the region where the rotator 52 is connected to the inner concentric tube 50, distally over the proximal end of the pusher tube handle 24. An annular space is provided between the rotator sleeve 50 and the inner connector tube 50, which receives a coil spring 60, one end of which is attached to the inner concentric tube 50 or rotator 52, and the other end of which is attached to the pusher tube 22 or pusher tube handle 24. The rotator 52 is capped at the proximal end by a cap 62.

The pusher tube 22 and inner concentric tube 50 are rotatable with respect to one another. This rotation is accomplished by rotating the rotator 52 in relation to the handle 24. The rotation biases and is therefore resisted by the coil spring 60.

Figure 3:
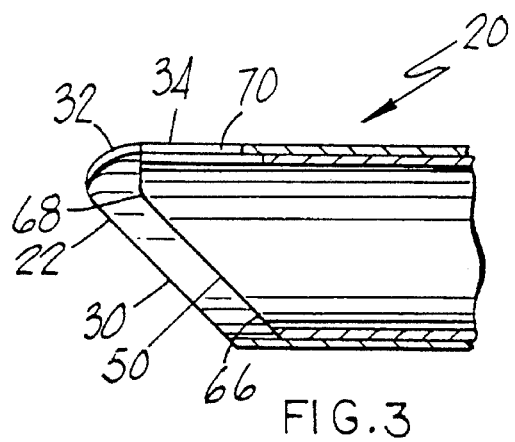
FIG. 3 shows a detailed-side sectional view of the distal end of the knot pusher assembly.
Figure 4:
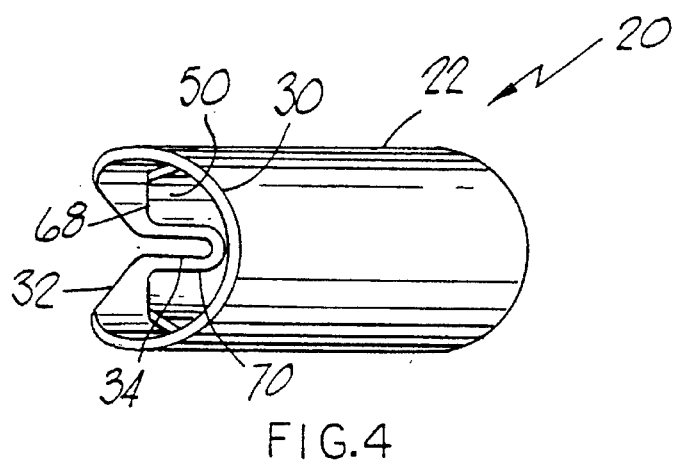
FIG. 4 shows a bottom view of the distal end of the knot pusher assembly.

The distal end of the knot pusher assembly 20 includes the distal ends of the pusher tube 22 and inner connector tube 50, which are better shown in the detail view of FIG. 3–6. FIG. 3 and FIG. 4 are detailed views showing the distal end of the pusher tube 22 and inner concentric tube 50. As can be seen, the distal end of the inner concentric tube 50 is slightly recessed from the distal end of the pusher tube 22. Moreover, the ends are specially shaped. The end of the pusher tube 20 has a bevel 30 on one side and has a indentation 32 on the opposite side. At the proximal extreme of the indentation 32 is a pusher tube slot 34 extending longitudinally toward the proximal end of the knot pusher assembly 20. The end of the inner concentric tube 50 includes a bevelled side 66 and a flat portion 68. Intermediate in the flat portion 68 is an inner concentric tube slot 70 which extends longitudinally toward the proximal end of the knot pusher assembly 20.

Figure 6:
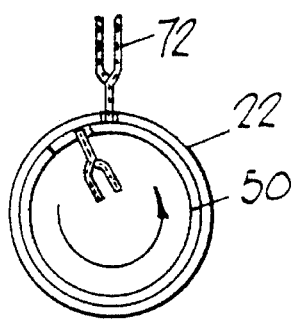
FIG. 6 shows an end view of the distal end of the knot pusher assembly cutting suture material.

The inner concentric tube slot 70 aligns with the pusher tube slot 34 when the inner concentric tube 50 is in its unrotated position in relation to the pusher tube 22, or in other words, when the spring 60 in the proximal end of the knot pusher assembly 20 (see FIG. 2) is unbiased. As shown in the end view of FIG. 6, when the inner concentric tube 50 is rotated in relation to the pusher tube 22 to bias the spring 60, the inner concentric tube slot 70 becomes unaligned with the pusher tube slot 34. In the aligned position of FIG. 5, the aligned slots 34 and 70 can receive a length of material 72. By rotating the inner concentric tube 50 in relation to the pusher tube 22, they become unaligned to thereby cut the material 72 as shown in FIG. 6.

Figure 7:
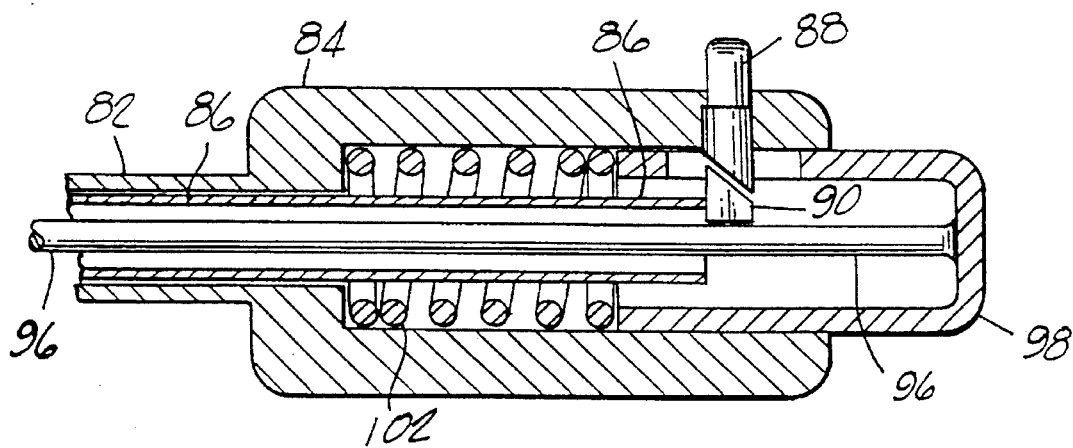
FIG. 7 shows a side sectional view of the proximal end of the plunger assembly of the present invention.
Figure 8:
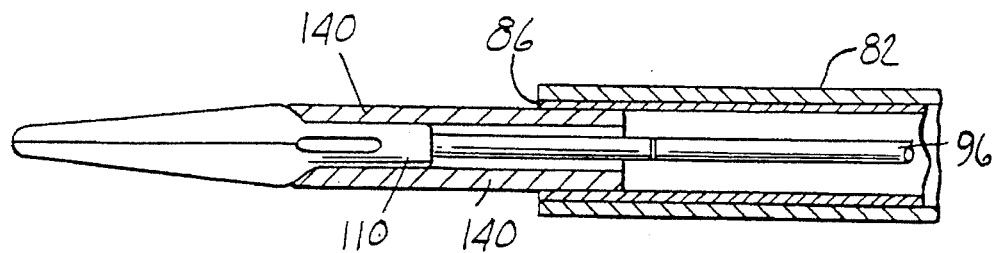
FIG. 8 shows a side sectional view of the distal end of the plunger assembly.

The plunger assembly 80 is shown in detail in FIGS. 7–8. The plunger assembly 80 includes a plunger shaft 82 which is a elongated tubular element. The proximal end of the plunger shaft 82 is attached to a plunger handle 84. Inside and concentric with the tubular plunger shaft 82 is a carrier releaser 86 which is also a tubular element. The distal end of the carrier releaser 86 coincides with the distal end of the plunger shaft 82. The proximal end of the carrier releaser 86 extends past the proximal end of the plunger shaft 82 and into the interior cavity of plunger handle 84 where it engages the mechanism of a carrier release button 88. The mechanism is any suitable arrangement which drives the carrier releaser 86 distally upon actuation of the carrier release button 88. In the embodiment shown, the proximal end of the carrier releaser 86 is attached to a ramp 90 which engages a sloped surface on the carrier release button 88. Thus by pushing the carrier release button 88 into the plunger handle 84, the sloped surface of the carrier release button 88 engages the ramp 90 at the proximal end of the carrier releaser 86 to drive the carrier releaser distally relative to the plunger shaft 82 and plunger handle 84. This distal displacement has the effect of protruding the distal end of the carrier releaser 86 past the distal end of the plunger shaft 82. The carrier releaser 86 may be biased toward the proximal end by a suitable spring (not shown) so that it returns proximally each time the carrier release button 88 is released.

Inside and concentric with the carrier release is a carrier holder 140 which is fixed in relation to the plunger shaft 82. Inside and concentric with the carrier holder 140 is a clamp holder 96 which extends from the distal end to the proximal end where it is attached to a clamp actuator 98. The clamp actuator 98 is a cylindrical element received by the plunger assembly handle 84. The clamp actuator 98 has a central cavity to contain the inner potion of the carrier release button 88 and the ramp 90 at the proximal end of the carrier releaser 86. The distal end of the clamp actuator 98 abuts against the end of a coil spring 102 contained within the plunger assembly handle 84 so that the clamp actuator 98 and attached clamp holder 96 are biased proximally.

Figure 9:
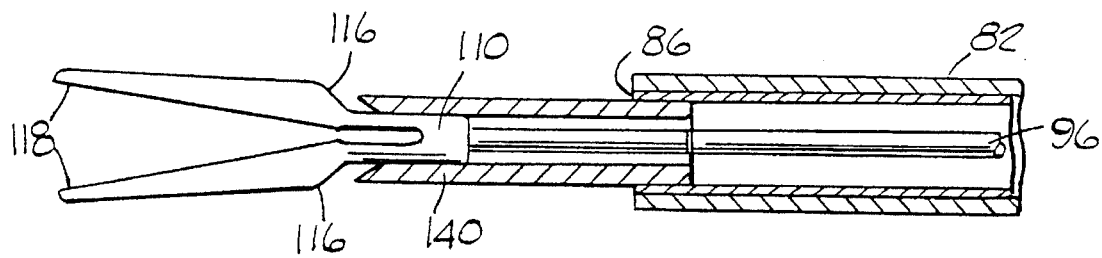
FIG. 9 shows a side sectional view of the distal end of the plunger assembly with the clamp jaws in their relaxed open position.

The distal end of the clamp holder 96 is attached to a spring clamp 110, better shown in FIGS. 8–9, in which the carrier is omitted for clarity. FIG. 8 shows the spring clamp 110 in the closed position, wherein the clamp holder 96 is positioned distally by the relaxed clamp actuator 98 so that the clamp holder 96 is retracted partially into the plunger assembly 80. The proximal retraction of the clamp holder 96 urges the sloped backs 116 of the clamp jaws 118 against the distal end of the carrier holder 86. The distal end of the carrier holder 140 thereby exert an axial force on the backs 116 of the clamp jaws 118, to urge the clamp jaws 118 shut. In FIG. 9, the clamp actuator 98 (see FIG. 7) has been depressed, to displace the clamp holder 96 and attached clamp jaws 118 distally. This causes the backs 116 of the clamp jaws 118 to protrude past the distal end of the carrier holder 140, thereby allowing the clamp jaws 118 to assume their normally open position.

Figure 10:
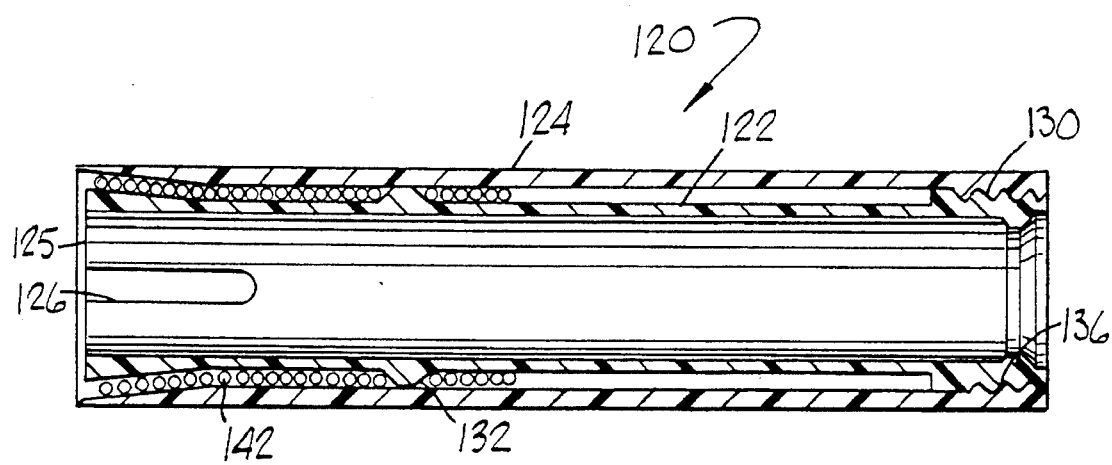
FIG. 10 shows a side sectional view of the knot carrier of the invention.

The carrier 120 is shown in detail in FIG. 10. The carrier 120 includes a spool 122 and a sheath 124 over the spool 122. The spool is a tubular element being flared at the distal end 125 with a plurality of longitudinally extending slots 126. The slots 126 allow for space for the flared distal end to deform radially inward to reduce the effective diameter and circumference of the distal end 125. At the proximal end of the spool 122 is a set of threads 130 on the radially outer surface. Between the distal end 125 and proximal end is a radially extending ring 132. A length of material and a knot, together 142, is rolled onto the spool 122 in the region between the extreme digital end 125 and the ring 132.

The sheath 124 is also a tubular element, concentric with the spool 122. At the distal end of the sheath, the radially inner surface is chamfered in the region overlying the flared distal end 125 of the spool. At the proximal end, the radially inner surface includes a set of threads 136 that mate with the threads 130 in the radially outer surface of the spool 122. The spool 122 and the sheath 124 are held together by the engagement of these respective threads 130 and 136.

A detail of the carrier 120 positioned on the plunger assembly 80 is shown in FIG. 11. As can be seen, the carrier 120 slides over the distal end of the carrier holder 140. The extreme distal end of the carrier holder 140 is dimensioned such that it exerts a radially outward force on the flared distal end 125 of the spool 122 of the carrier holder 120. This radially outward force deforms the flared distal end 125 of the spool 122 radially outward to bind the material and knot 142 that is rolled onto the spool 122, between the spool 122 and the sheath 124.

Figure 12A:
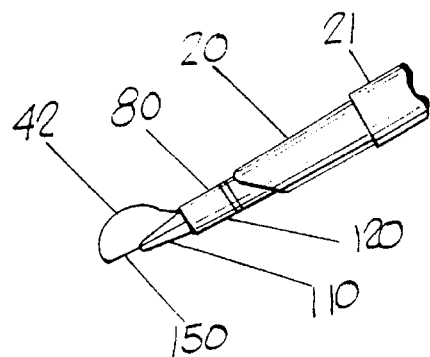
Figure 12B:
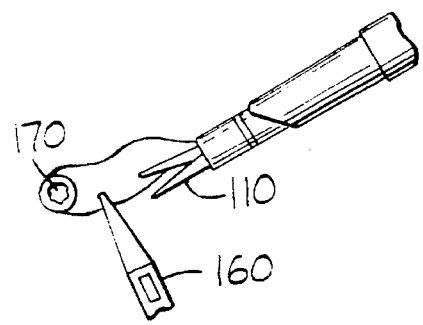
Figure 12D:
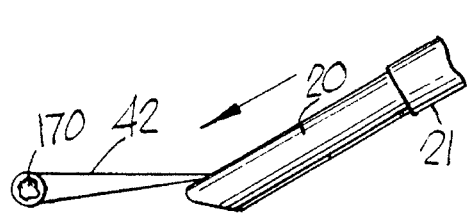
Figure 12C:
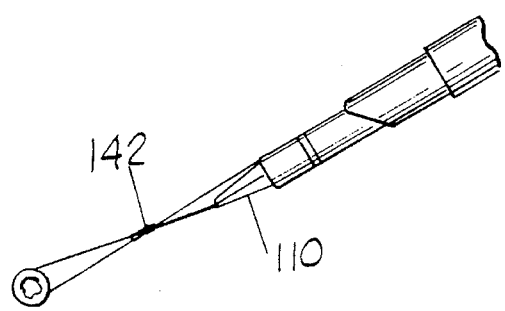
Figure 12:
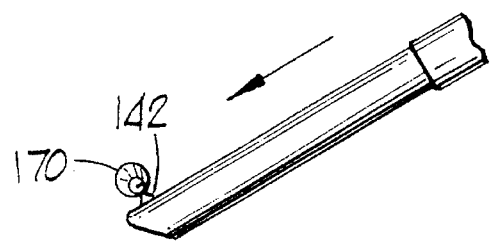
FIG. 12 shows a side sectional view of the distal end of the invention showing the knot carrier in the releasing position.
Figure 12:

FIG. 12 shows the carrier 120 being released from the carrier holder 140. As explained above, the carrier 120 can be pushed partly off the carrier holder 84 by actuating the carrier release button 88 (see FIG. 7) to protrude the carrier releaser 86 distal end past the plunger shaft 82 distal end. This causes the flared distal end 125 of the carrier 120 to extend past the distal end of the carrier holder 140, thereby allowing the flared distal end 125 of the carrier 120 to relax and contract radially. This relieves the binding force between the spool 122 and the sheath 124 so that the material 142 can come out of the carrier 120.

The operation of the device is shown in FIGS. 12A–12F. As shown in FIG. 12A, the knot pusher assembly 20 is inserted into a cannula 21 prior to the plunger assembly 80 being inserted into the knot pusher. This ensures the safety and security of the needle and suture during their insertion. The carrier 120 is then placed over the clamp 110 and onto the carrier 140. A needle 150 is previously attached to the suture material 142. The carrier 120 is then secured in the clamp 110, and the plunger assembly 80 is inserted into the knot pusher assembly 20.

As shown in FIG. 12B, the needle 150 is taken from the clamp 110 by another instrument 160 (such as a needle holder or clamp) passing through another cannula. The needle 150 is passed through or around a feature, such as through tissue or around a vessel 170, and handed back to the clamp 110. As shown by FIG. 12C, the knot and material 142 is released from the carrier 120 by actuating the carrier release 86 to protrude the carrier 120 past the distal end of the carrier holder 140 so that the flared distal end 125 of the carrier spool 122 relaxes radially inward to relieve the binding on the knot and material 142 (see FIG. 12). This releasing of the knot and material provides the necessary slack in the material to accomplish the suturing or tying. The releasing of the knot allows the knot to lightly cinch down on the lead end of the material which is now grasped by the clamp 110.

As shown in FIG. 12D, pulling on the plunger assembly within the knot pusher assembly 20 while pushing on the knot pusher assembly 20 retracts and tensions the leads of the material 140 which allows the knot pusher assembly 20 to engage the leads. Specifically, the leads pass into the aligned pusher tube slot 34 and inner concentric tube slot 70 (see FIG. 4). Continued pulling on the plunger assembly 80 while pushing on the knot pusher assembly 20 tightens and drives the knot 142 into position against the vessel 170 to tightly tie the vessel 170.

The leads of material 140 may then be cut, either immediately adjacent to the knot or away from the knot to leave longer loose ends as desired. The cutting is accomplished by positioning the knot pusher assembly 20 at the cutting site, still with the material in the aligned pusher tube slot 34 and inner concentric tube slot 70 (see FIG. 4 again). The inner concentric tube 50 is then rotated in relation to the pusher tube 22 (see FIG. 6) by rotating the rotator 52 while grasping the handle 24 (see FIG. 2) to unalign the pusher tube slot 34 and the inner concentric tube slot 70. This leaves a tied knot on a vessel 170 as shown in FIG. 12F.

The plunger assembly 80 is then withdrawn from the knot pusher assembly 20, and the carrier 120 and material leads including the needle are discarded. The instrument is then ready to be reloaded with a new carrier 120 and needle for tying the next knot or suture.

What is claimed is:

1. An assembly for use in surgery, comprising a suture knot pusher tube having a distal end slot; and an inner concentric tube positioned within the pusher tube having a distal end slot, the pusher tube and inner concentric tube being moveable with respect to one another to align or unalign said slots, whereby a suture can be cut by placing it into the aligned slots and then misaligning the slots by moving the pusher tube and inner concentric tube with respect to one another, and wherein the pusher tube and inner concentric tube are biased with respect to one another to align said slots.

2. An assembly for use in surgery, comprising a suture knot pusher tube having a distal end slot; and an inner concentric tube positioned within the pusher tube having a distal end slot, the pusher tube and inner concentric tube being moveable with respect to one another to align or unalign said slots, whereby a suture can be cut by placing it into the aligned slots and then misaligning the slots by moving the pusher tube and inner concentric tube with respect to one another, wherein said assembly is for use with sutures of a particular diameter, and the slots are sized such that they will receive said sutures but will not receive a knotted said suture.

3. An assembly for use in surgery, comprising a suture knot pusher tube having a distal end slot; and an inner concentric tube positioned within the pusher tube having a distal end slot, the pusher tube and inner concentric tube being moveable with respect to one another to align or unalign said slots, whereby a suture can be cut by placing it into the aligned slots and then misaligning the slots by moving the pusher tube and inner concentric tube with respect to one another, wherein at least one of the pusher tube and inner concentric tube includes a distal end with one side chamfered toward the slots.

* * * * *